United States Patent [19]

Wolfram et al.

[11] Patent Number: 5,036,012

[45] Date of Patent: Jul. 30, 1991

[54] BIODEGRADATION OF LIQUID SCINTILLATION COCKTAILS

[76] Inventors: James H. Wolfram, 1263 Londonderry, Idaho Falls, Id. 83404; Robert D. Rogers, 1206 Norton St., Idaho Falls, Id. 83402

[21] Appl. No.: 366,744

[22] Filed: Aug. 14, 1989

Related U.S. Application Data

[62] Division of Ser. No. 117,028, Nov. 3, 1987, Pat. No. 4,863,872.

[51] Int. Cl.$^5$ .............................................. C02F 3/34
[52] U.S. Cl. .................................... 435/262; 435/264; 435/874
[58] Field of Search ............................... 435/262, 264

[56] References Cited

U.S. PATENT DOCUMENTS

| | | | |
|---|---|---|---|
| 4,352,886 | 10/1982 | Pillis et al. | 435/877 |
| 4,452,894 | 6/1984 | Olsen et al. | 435/262 |
| 4,493,895 | 1/1985 | Colaruotolo et al. | 435/874 |
| 4,535,061 | 8/1985 | Chakrabarty et al. | 435/262 |

OTHER PUBLICATIONS

Claus, D. et al., "The Decomposition of Toluene by Bacteria", *Journal of General Microbiology*, 1964, pp. 107–122.
Finette, Barry A. et al., "Isolation and Characterization of *Pseudomonas putida* PpF1 Mutants Defective in the Toluene Dioxygenase Enzyme System", *Journal of Bacteriology*, vol. 160, No. 3, Dec. 1984, pp. 1003–1009.
Furukawa, Kensuke et al., "Common Induction and Regulation of Biphenyl, Xylene/Toluene, and Salicylate Catabolism in *Pseudomonas paucimobilis, Journal of Bacteriology*", vol. 154, 1983, pp. 1356–1362.
Gibson, David T., "Microbial Transformations of Aromatic Pollutants," *Aquatic Pollutants: Transformation and Biological Effects*, Proceed 2nd International Symposium on Aquatic Pollutants, Sep. 1977, pp. 187–204.
Gibson, David T. et al., "Degradation of Aromatic Hydrocarbons", *Microbial Degradation of Organic Compounds*, pp. 192–197.
Gibson, David T. et al., "Bacterial Metabolism of para-meta-Xylene: Oxidation of the Aromatic Ring", *Journal of Bacteriology*, vol. 119, No. 3, Sep. 1974, pp. 930–936.
Kunz, Daniel A. et al., "Catabolism of Pseudocumene and 3-Ethyltoluene by *Pseudomonas putida* (arbella) mt-2: Evidence of New Functions of the TOL (pWWO) Plasmid", *Journal of Bacteriology*, vol. 146, No. 1, Apr. 1981, pp. 179–191.
Kunz, Daniel A. et al., "Isolation and Characterization of Spontaneously Occurring TOL Plasmid Mutants of *Pseudomonas putida* HS1", *Journal of Bacteriology*, vol. 146, No. 3, Jun. 1981, pp. 952–964.
Tobak, Henry H. et al., "Biodegradability Studies with Organic Priority Pollutant Compounds", *Journal WPCF*, vol. 53, No. 10, Oct. 1981, pp. 1503–1518.

*Primary Examiner*—Sam Rosen
*Attorney, Agent, or Firm*—Robert A. de Groot; Stephen A. Gratton

[57] ABSTRACT

An apparatus for the biodegradation of toxic organic solvents contained in liquid scintillation cocktail (LSC) wastes is disclosed, as well as a method for its operation. Additionally, a novel microorganism, Pseudomonas sp NRRL B-18435, is disclosed for the biodegradation of the organic solvents contained in such wastes. The apparatus is capable of operating with solvent concentrations greater than 5,000 ppm and emulsifier concentrations greater than 2,000 ppm. Rates of solvent biodegradation range from 0.095 mg/L.min to about 7.0 mg/L.min.

4 Claims, 6 Drawing Sheets

BIODEGRADATION OF LIQUID SCINTILLATION COCKTAILS

This is a division of application Ser. No. 07/117,028, filed Nov. 3, 1987, now U.S. Pat. No. 4,863,872.

BACKGROUND OF THE INVENTION

The present invention relates to the biodegradation of a liquid scintillation cocktail (LSC) having high concentrations of both organic solvents and emulsifiers. In a preferred embodiment, the biodegradation is effected by a microorganism identified as Pseudomonas sp NRRL B-18435. A deposit of this microorganism has been made in the Northern Regional Research Center, U.S. Department of Agriculture, in Peoria, Ill., and is available under conditions set forth under 37 CFR.

LSC waste solutions are generated in a broad range of medical and biotechnological environments. For instance, when it is desired to trace a particular molecule or compound through a metabolic pathway, it is frequently useful to tag the compound or molecule under consideration with a isotope, such as tritium, C-14, S-35 or P-32. When analyzing the end result of the experiment, the presence (or quantity) of the tagged molecule can be detected by a liquid scintillation counter. Such counters detect fluorescence of introduced chemicals (fluor) resulting from the low energy beta particle emission from the tagged molecule. This reaction occurs in a "liquid scintillation cocktail", or LSC, which typically contains one of the following solvents: toluene, p-xylene, 1, 2, 4-trimethyl benzene (pseudocumene), benzene, dioxane or cyclohexane. Other organic solvents may be found in the LSC.

Waste LSC solutions containing any of the above solvents are considered mixed hazardous wastes because they contain both radioactive and toxic organic compounds. Under current Environmental Protection Agency (EPA) regulations, many waste generators are forced to store these solutions because current waste handling facilities are not permitted to accept them. It is estimated that world-wide usage of all LSC materials result in the generation of between 300,000 and 1 million gallons of waste per year, approximately one-third of which is produced in the United States. The current cost to the use of such liquids is about evenly divided between the purchase price and the disposal or storage cost. Other than long-term storage, incineration (at a very limited number of sites and at high cost) is the only disposal option.

In addition to the organic solvents, LSC liquids typically contains a relatively high quantity of emulsifier and a relatively small quantity of flourescing agents. Typical emulsifiers include Triton-X 100 ® and other similar compounds sold by Rohm and Haas. Generally speaking, the LSC contains about 70% organic solvent and about 30% emulsifier. Flourescing agents include Eastman Kodak's bisMSB and PPO.

Microbial degradation of toluene, xylene and pseudocumene has been demonstrated by *Pseudomonas putida* and *P. paucimobilis*. However, such biodegradation has been demonstrated to occur only in a batch type process, and only with relatively low concentrations of the organic solvents. Thus far, a viable continuous process utilizing a microorganism capable of long-term exposure to such solvents has not been available, especially in the presence of high levels of emulsifiers.

The concentration of the total organic solvents in a stored quantity of the LSC will typically be on the order of from about 50% to about 90% of the solution, with the emulsifier comprising from about 10% to about 50% of the solution. Most commonly, the LSC solution contains organic solvent and emulsifier in a proportion of about 70:30. In the biodegradation of LSC, it would be advantageous to be able to use such stored liquids without the necessity of undergoing a substantial dilution to avoid microorganism toxicity, which would increase both the time necessary for biodegradation and the size of the bioreactor.

The advantages of a continuous bioreactor or chemostat, as opposed to a batch-type reactor, can be significant. A continuous bioprocessing system can maintain the optimum conditions for living cells. Since the microorganisms are the catalysts in the process, optimum conditions enable maximum rates of biodegradation. Factor contributing to the advantages of continuous processing include: maintenance of high viable cell densities; optimum substrate concentrations, and continuous removal of by-products which can inhibit further degradation. Additionally, a continuous process offers a significant manpower and cost savings in that it ca be "turned on" and thereafter substantially ignored. By contrast, batch-type process require regular monitoring of microbial viability and consequent biodegradation, as well as periodic recharging of the bioreactor with nutrients, microorganisms and LSC waste product to be degraded.

Therefore, there is a need among users of LSC for an LSC waste-treatment unit which operates on a continuous basis, produces non-toxic effluent, and is capable of digesting relatively high concentrations of the organic LSC solvents, especially in the presence of high levels of emulsifier.

SUMMARY OF THE INVENTION

The present invention comprises an apparatus, and method of utilizing the apparatus, for the biodegradation of liquid scintillation (LSC) wastes. While the method can be practiced with both batch and continuous bioreactors, the continuous process utilizing the continuous chemostat reactor is preferred. Most preferably, the process is practiced with Pseudomonas, sp NRRL B-18435 as the catalyst to effect biodegradation of the LSC.

LSC wastes containing organic solvents, usually benzene-ring or substituted benzene-ring compounds, emulsifiers and fluorescing compounds are produced in sufficient quantities by large numbers of users to create disposal problems. On-site biodegradation would render such compounds non-toxic and could be disposed of locally. However, heretofore such bioreactors have not been possible due to the fact that microorganisms have not been identified which are capable of withstanding the high organic solvent and emulsifier concentrations present in such wastes. Additionally, a system for continuous operation of such LSC bioreactors has not been available.

Therefore, the apparatus of the present invention comprises a bioreactor, either in a batch or chemostat environment, wherein biodegradation of LSC wastes can occur. The bioreactor is operated under conditions conducive to biodegradation of LSC wastes which are introduced either directly or by volatilization (the organic solvent only being introduced into the bioreactor). A microorganism has been identified capable of biodegrading organic solvents present in concentrations greater than 5,000 ppm, in the presence of emulsifier as high as 2,150 ppm. Rates of biodegradation are not adversely affected at relatively low emulsifier concentrations; at high emulsifier concentrations they are decreased but are still at commercially practicable levels.

DETAILED DESCRIPTION OF THE INVENTION

Figure 1:
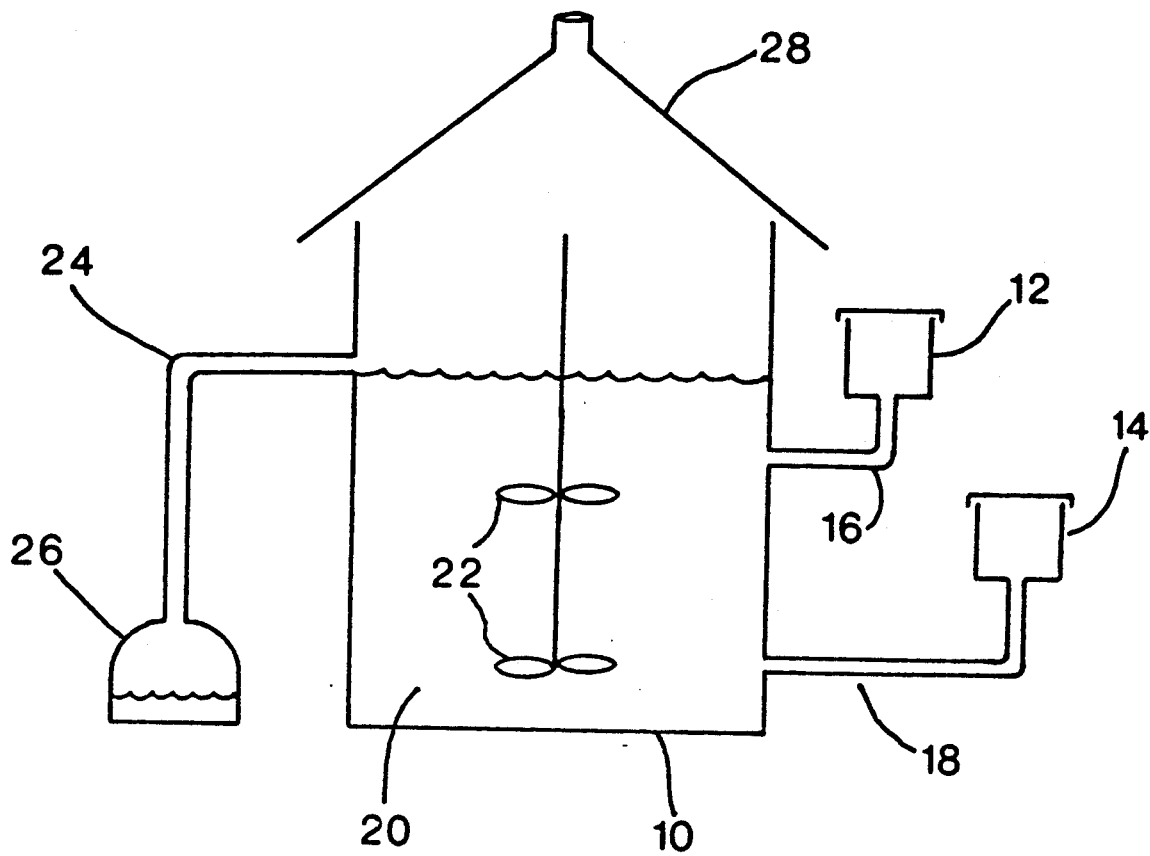
FIG. 1 is a schematic representation of a bioreactor of the present invention.

As shown schematically in FIG. 1, there is a chemostat (or bioreactor), generally designated 10, a mineral salts nutrient media reservoir 12, an LSC collection and storage unit 14, each with appropriate conduits 16, 18 respectively, which may be provided with valves, pumps and other means of assuring uniform introduction of the various fluids into the bioreactor. As illustrated, the only carbon source available to the microorganisms in the bioreactor are the organic solvents contained in the LSC. The broth 20 within the bioreactor 10 is agitated and aerated by suitable means, illustrated in FIG. 1 by conventional rotating paddles 22. Excess biomass production and fluid input not utilized by the microorganisms ca be decanted from the bioreactor, as by conduit 24 and directed to a storage unit 26. The removal of fluids and by-products through conduit 24 may result in the unintended removal of toxic organic solvents contained in the LSC. However, a small quantity of living microorganisms will inevitably be removed at the same time so that, in the event any appreciable toxic material is decanted into unit 26, microorganisms present therein will rapidly biodegrade the organic solvent, rendering it non-toxic. In the event that the aeration of the broth results in the volatilization of toxic materials out of the broth, a hood 28 can be provided over the bioreactor 10 to collect any such airborne contaminants. If such airborne contamination is observed to be a problem, the airstream exiting the top of hood 28 can be redirected into the unit 14 or into the broth 20. Alternatively, the bioreactor may be fitted with a condenser to remove any airborne solvents escaping therefrom, which may thereafter be reintroduced into unit 14 or the bioreactor 10. Because most of the microorganisms useful in such reactors are aerobic, it may be advantageous to inject additional oxygen into the bioreactor if an oxygen deficiency is observed.

While it is believed that there may be other microorganisms which will function in the apparatus of the present invention, applicants have isolated a species of Pseudomonas from oil-laden soil adjacent oil storage tanks at an industrial site which appears to have superior biodegradation.

A large number of microorganisms were isolated using an enrichment technique comprising a mineral salts broth with xylene and or toluene supplied to the broth via volatilization as a carbon source. Most of the isolates showed little or no viability in this environment, however growth of a few isolates occurred within two to three days, at which time mineral salt agar plates were used to isolate pure colonies. A desiccator saturated with a xylene or toluene atmosphere was used as the incubation chamber. A number of the colonies which appeared to maintain at least minimal growth characteristics under such conditions were tested in a batch-type bioreactor, and later in a chemostat. A number of the isolates functioned minimally in the batch reactor, and it was believed at the time that, based on the published literature, there was little reason to believe they would perform differently in a continuously-operated chemostat. Much to applicant's surprise however, one of the isolates functioned significantly better in the chemostat than it had in the batch reactor. This isolate is now identified as Pseudomonas sp NRRL B-18435, and the taxonomic criteria are set forth in Table 1. Because the bacteria was isolated from soil, as opposed to being obtained from known cultures, the organism is not identified more specifically than Pseudomonas sp.

TABLE 1

| | | | | Characterization of Pseudomonas sp NRRL B-18435* | | | | | | | | |
|---|---|---|---|---|---|---|---|---|---|---|---|---|
| Oxi-dase | Anaerobic dextrose | Arginine dehydrolase | $N_2$ gas production | $H_2S$ | In-dole | Xy-lose | Aerobic dextrose | Urea | Ci-trate | Gram stain | Cell mor-phology | Emulsifier resis-tance at 1500 ppm | Mo-tility |
| + | − | + | + | − | − | + | + | − | + | − | rods | + (no morbidity) | + |

*colony morphology on:

peptone — glucose-yeast extract agar } small, round, shiny,
nutrient agar + glucose } smooth, yellowish on clear mineral salts media, with a pH between 5.9 and 6.9, and under a saturated atmosphere of solvent, colonies produce a greenish-yellow fluorescent pigment into media The presence of an emulsifier has a severely deleterious effect on the cell morphology of many microbiological systems. It is believed that when present in concentrations as low as 50 ppm, emulsifiers such as Triton-X 100 typically disrupt the cell wall, resulting in either complete or partial reduction in biochemical processes occurring within the cell. Surprisingly, applicant has found that the preferred Pseudomonas sp identified herein can function adequately in the presence of about 1500 ppm, concentrations which might be expected in a chemostat broth loaded with LSC wastes.

Additionally, few microorganisms that function adequately in a batch mode will be expected to function adequately in a continuous process. Early experimental tests conducted by applicant indicated that Pseudomonas sp NRRL B-18435 not only loses its viability over time in a batch process, but also exhibits a gradually decreasing ability to degrade the organic solvents present in LSC. Neither of these observations are evident in the same organism when operated in a continuous mode.

Two methods of introducing the LSC to the bioreactor are readily available: volatilization and direct injection. Volatilization requires that the organic solvents in the LSC be volatilized (as by bubbling air therethrough) with the resulting airborne solvents being directed into the broth in the bioreactor. Alternatively, the LSC can be directly injected or introduced into the bioreactor broth. In some cases it may be desirable to utilize the volatilization method, so as to inject only the carbon source into the bioreactor, and not any ancillary material. For instance if the microorganism exhibits sensitivity to a particular emulsifier, volatilization would be the method of choice to introduce the solvents to the bioreactor, since the emulsifiers would not be volatile.

While a number of different bioreactor models are available (such as continually stirred tank, air lift, trickling bed and fluidized bed) the continually stirred tank reactor was chosen by applicant because of its ready availability, ease of operation and technician familiarity. However, if very high cell densities are desired, the fluidized bed reactor may be preferable. Likewise, if maximum diffusion of gaseous substrates is desired, the airlift design may be preferable.

There is believed to be no practical lower limit for the efficacy of this process relative to concentration of organic compounds (depending upon the quantity of LSC to be biodegraded and the time available), but a low level of carbon source will have a limiting effect on the growth and replication rate of the microorganism. Therefore, it is believed that a commercial process must have a microorganism density of at least $10^7$ cells/ml, while a carbon source concentration of approximately 1 ppm will maintain the microorganisms in a viable condition. However, it is believed that a carbon source concentration of at least approximately 100 ppm will be required to operate the invention in a continuous, commercially practicable manner. The upper limit of the toxic solvent concentration has not been determined precisely, but is in excess of 5,000 ppm. It is believed that with the microorganism Pseudomonas sp NRRL B-18435 the upper limit of commercial practicability is between about 5,000 and 10,000 ppm.

Applicant has identified the microorganism of choice as Pseudomonas sp, having the characteristics set forth in Table 1. Additionally, applicant has deposited in the permanent collection of the Northern Regional Research Laboratory, U.S. Department of Agriculture, Peoria, Ill., U.S.A., a culture of the preferred Pseudomonas sp, and it is designated therein as Pseudomonas sp NRRL B-18435. Subcultures of this microorganism are available from this depository by request made thereto. It should be understood that the availability of the culture does not constitute a license to practice the invention in derogation of patent rights granted hereby. While applicant has designated Pseudomonas sp NRRL B-18435 as the best mode of practicing the invention, there may be other as yet unidentified microorganisms which will function to some degree in the apparatus and process of this invention. Applicant's designation of Pseudomonas sp NRRL B-18435 is not intended to infer that it is the sole microorganism operative in this invention.

EXAMPLE 1

In order to determine the viability of a number of different microorganisms when grown with a solvent carbon source and isolated as set forth above, a mineral salt media having the following composition:
$NH_4NO_3$—1 g/L
$MgSO_4.7H_2O$—0.7 g/L
$KH_2PO_4$—0.7 g/L
$K_2HPO_4$—0.7 g/L
Micronutrients:
0.5 mg NaCl
2.0 mg $FeSO_4.7H_2O$
2.0 mg $MnSO_4$
1.0 mg $Na_2MoO_4$
was inoculated with unidentified stock culture microorganisms and permitted to grow unrestricted. To this media was added the carbon source, namely toluene or xylene, until a concentration of about 240 ppm of toluene or xylene was reached. The broth was agitated in a closed serum bottle. The batch was maintained under ambient temperature with an initial pH of 6.5.

After growth under a xylene or toluene atmosphere, three samples were chosen for further testing to determine optimum biodegradation of organic solvents. These samples are identified in FIGS. 2 and 3 as AMOL, X1 and X2. It can be seen in FIG. 2 that the toluene concentration of about 240 ppm was reduced to between about 15 to 100 ppm after 8 days. Similarly, as shown in FIG. 3, xylene concentration was reduced from about 240 ppm to about 0-90 ppm by the three microorganisms. Initial cell density in both cases was about $10^6$ cells/ml. It is to be understood that this test was merely an initial test to illustrate biodegradation of the organic solvent to select candidates for further testing; the system was not optimized for solvent biodegradation. As a result of these preliminary viability test, sample X2 was chosen for further testing.

EXAMPLE 2

Figure 2:
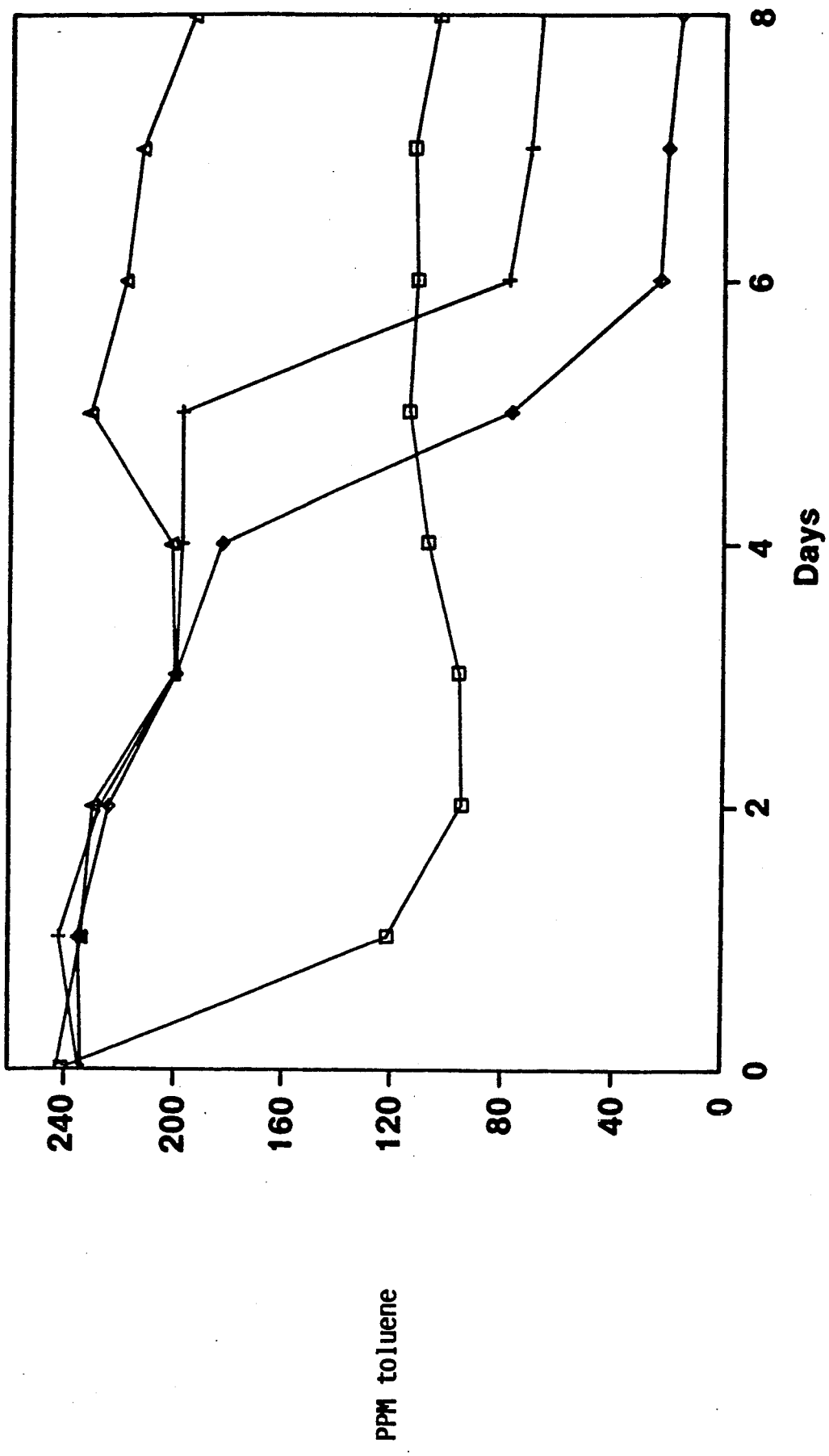
FIG. 2 is a graph illustrating toluene biodegradation by various microorganisms.
Figure 3:
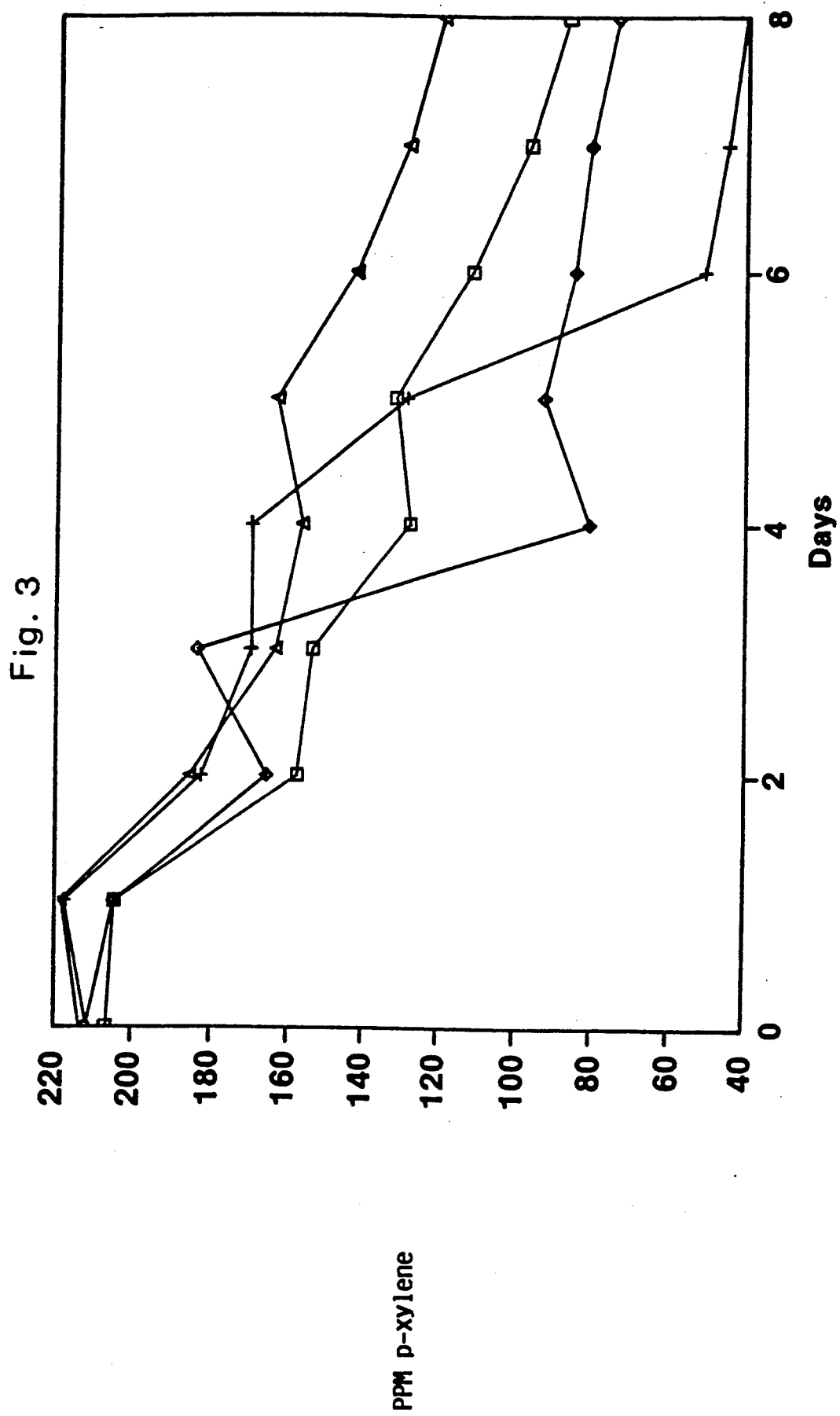
FIG. 3 is a graph illustrating p-xylene biodegradation by various microorganisms.
Figure 4:
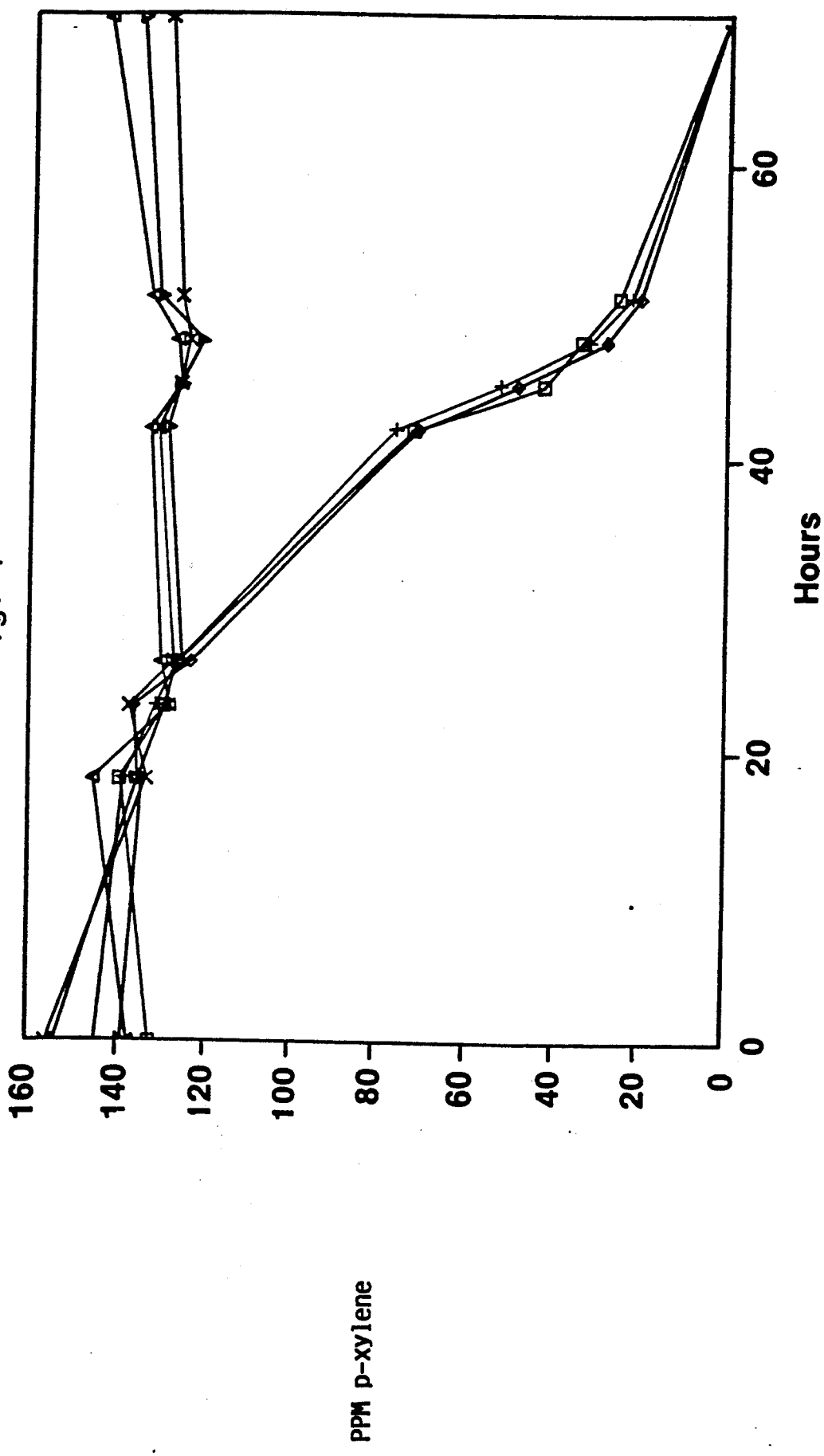
FIG. 4 is a graph illustrating p-xylene biodegradation by a preferred microorganism from a stock culture.

Sample X2 from FIGS. 2 and 3 was chosen for further biodegradation analysis. Replicate 2.0 ml samples of the microorganism, later identified as Pseudomonas sp NRRL B-18435, were taken from a stock culture and introduced into a sealed 100 ml serum bottle containing 20 ml of a p-xylene saturated mineral salts media. Initial cell density was estimated to be about $10^7$ cells/ml. The p-xylene concentration was reduced to zero after about 70 hours. Cell growth was observed by dramatically increased turbidity in the serum bottle. As can be seen in FIG. 4, after an initial growth or acclimatization period, biodegradation of xylene proceeded at a relatively rapid rate, given the low cell concentration.

EXAMPLE 3

Figure 5:
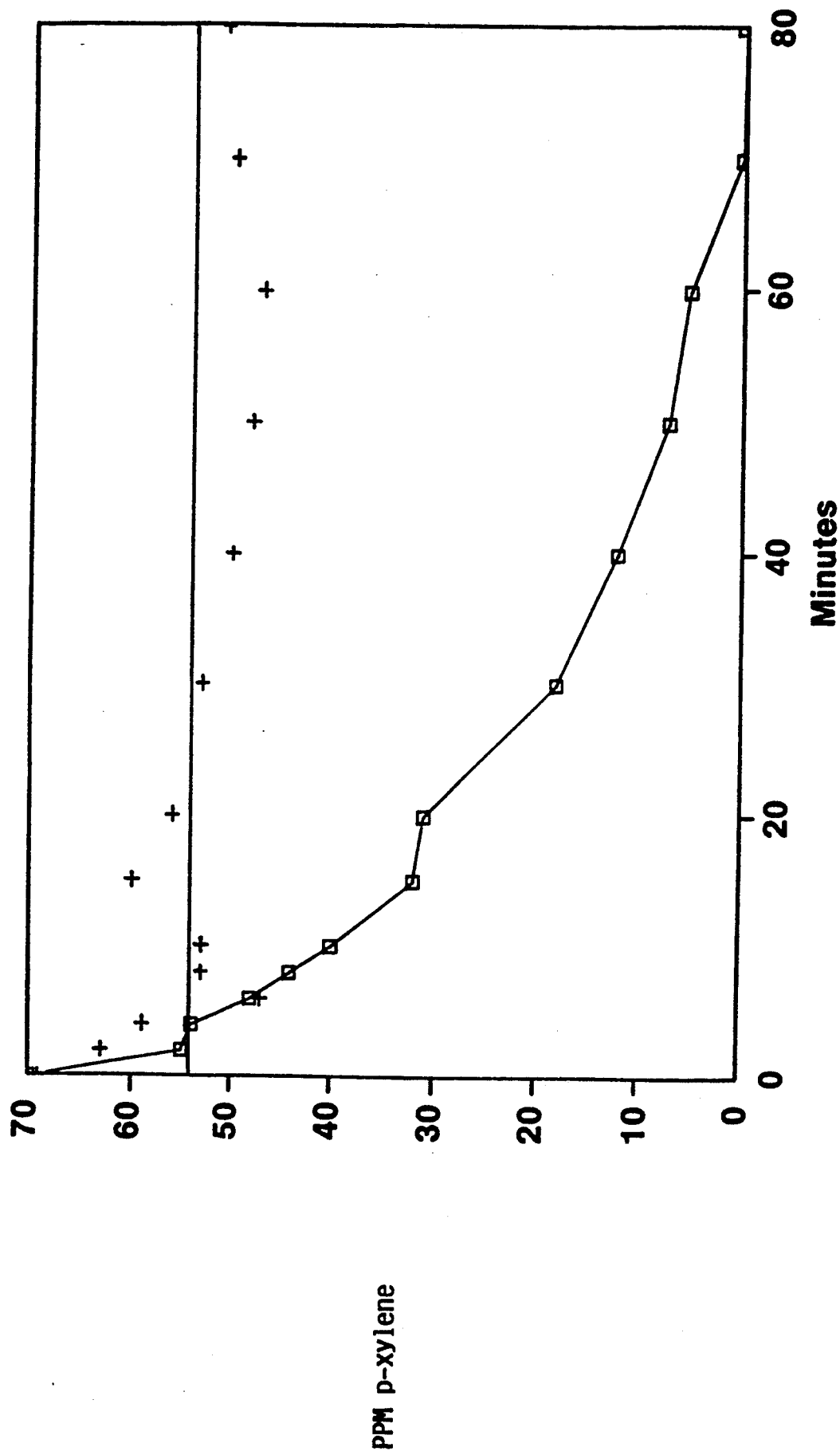
FIG. 5 is a graph illustrating p-xylene biodegradation by a preferred microorganism from a chemostat.

A chemostat was established as shown in FIG. 1, and maintained with a Pseudomonas sp NRRL B-18435 cell concentration of between about $10^8$ and $10^9$ cells/ml. The carbon source (p-xylene) concentration in the chemostat was introduced via volatilization at 4 ml/hr and maintained in the broth at about 100-200 ppm. At ambient (25° C.) temperature, and a pH of 6.0, agitation was provided at 300 ppm and an aeration rate of 20 ml/sec. Twenty milliliter samples were removed from the chemostat and placed in sealed 100 ml serum bottles. One milliliter samples were removed therefrom and killed with mercuric chloride. Initial cell density of the sample was about $10^8$ cells/ml. As shown in FIG. 5, the p-xylene concentration was reduced from about 70 ppm to zero in about 70 minutes.

EXAMPLE 4

Figure 6:
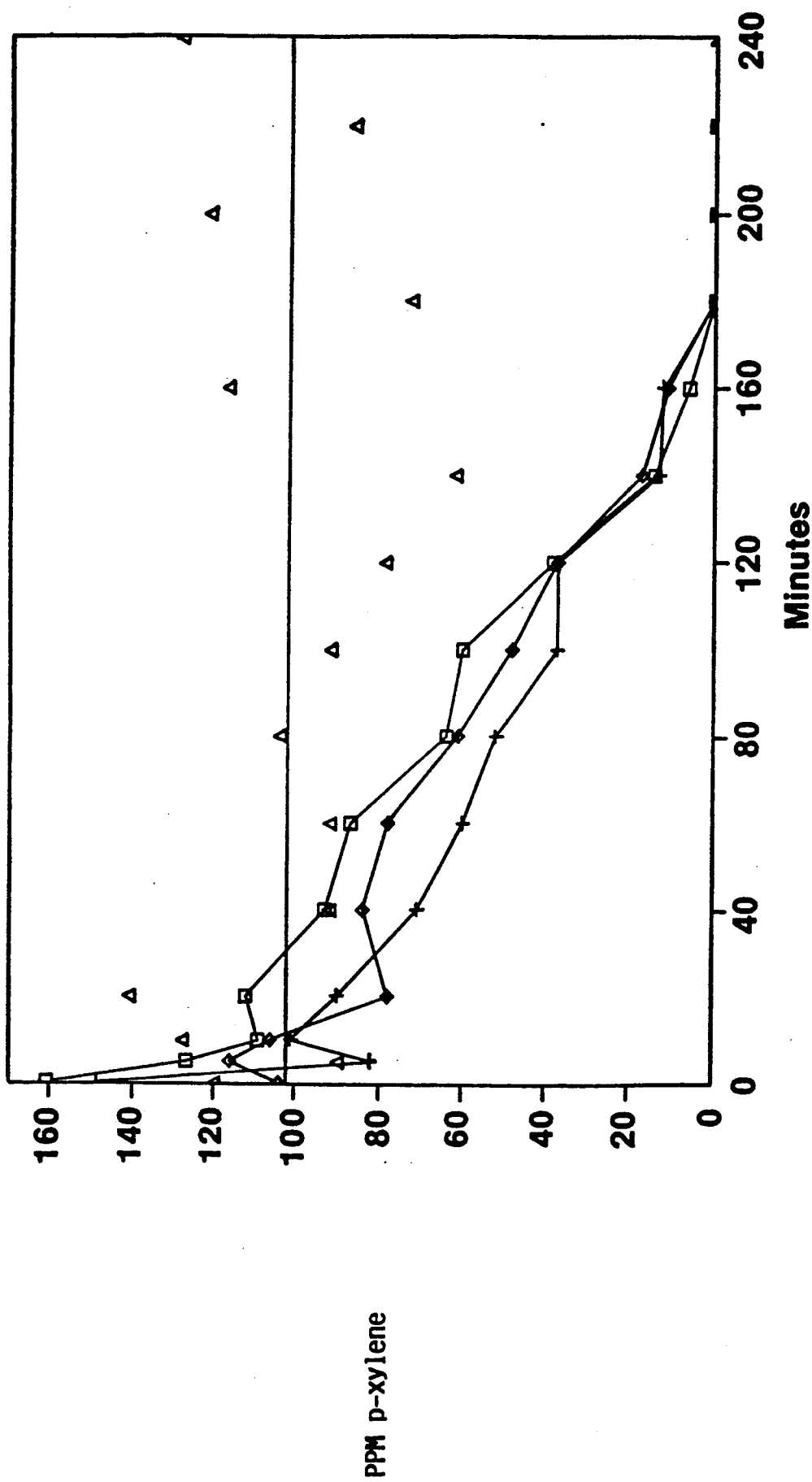
FIG. 6 is a graph illustrating p-xylene biodegradation by a preferred microorganism from a chemostat in the presence of emulsifiers.

In order to determine whether the preferred microorganism (Pseudomonas sp NRRL B-18435) was operative in the biodegradation of an LSC, 35 ml samples from the chemostat of Example 3 were placed in a sealed 100 ml serum bottle and purged of xylene by permitting the microorganisms to biodegrade the xylene from the chemostat to zero. The bottle was then spiked with an LSC comprising 300 ppm p-xylene, about 130 ppm emulsifier (Triton-X 100 ®) and less than 5 ppm of a fluorescing agent. The initial microorganism concentration was between about $10^8$ and $10^9$ cells/ml. One milliliter samples were withdrawn from the serum bottle and poisoned prior to analysis. Replicate samples shown in FIG. 6 illustrate that the microorganism Pseudomonas sp NRRL B-18435 is capable of completely degrading about 160 ppm p-xylene in about 3 hours, in the presence of about 130 ppm emulsifier.

EXAMPLE 5

In order to determine the rate of organic solvent biodegradation in high levels of solvent, 35 ml samples were withdrawn from the chemostat of Example 3, purged of xylene and placed in a sealed 100 ml serum bottle. Increasing amounts of an LSC was added to result in the desired solvent concentration. Samples were withdrawn and measured over a 1,000 minute period. As shown in Table 2, the rate of p-xylene degradation by Pseudomonas sp NRRL B-18435 actually increases as the p-xylene concentration increases to 5,000 ppm. The toxic concentration of solvent is as yet undetermined, but is between 5,000 ppm and 10,000 ppm. As noted in Table 2, the concentration of emulsifier present at the higher solvent concentration is extremely high, yet the microorganism is degrading the solvent at a commercially practicable rate.

TABLE 2

|  | Carbon Source | Carbon Source Concentration | Emulsifier Concentration | Degradation RATE (mg/L · min) |
| --- | --- | --- | --- | --- |
| BATCH | p-xylene | 160 ppm | — | 0.095 |
| CHEMOSTAT | p-xylene | 70 ppm | — | 5.0–6.0 |
|  | LSC | 500 ppm | 215 ppm | 0.7 |
|  | LSC | 1,000 ppm | 430 ppm | 0.8 |
|  | LSC | 5,000 ppm | 2,150 ppm | 1.0–3.0 |
|  | LSC | 10,000 ppm | 4,300 ppm | (Viability observed, but rate too slow to measure) |

The foregoing is considered as illustrative only of the principles of the invention. Further, since numerous modifications and changes will readily occur to those skilled in the art, it is not desired to limit the invention to the exact apparatus and process shown and described, therefore all suitable modifications and equivalents may be resorted to falling within the scope of the invention.

We claim:

1. A process for the biodegradation of waste liquid scintillation cocktail (LSC) having a radioactive isotope and comprising from about 50% to about 90% organic solvent compounds selected from the group consisting of p-xylene, 1-, 2-, 4-trimethyl benzene (pseudocumene), benzene, and toluene and from about 10% to about 50% emulsifier, the process comprising the steps of:
   a. introducing a metabolically acceptable mineral salts media into a bioreactor;
   b. inoculating the bioreactor with an effective amount of microorganism Pseudomonas sp NRRL B-18435 capable of metabolizing the organic solvent compounds and capable of withstanding the toxic effects of the emulsifier;
   c. introducing organic solvent compounds into the bioreactor and maintaining the concentration of organic solvent compounds therein at a level sufficient to supply the microorganism with a sole and adequate carbon source, and below the toxic limit of organic solvent compounds;
   d. agitating and aerating the mixture of mineral salts media, microorganism and organic solvent compound; and
   e. maintaining the bioreactor at conditions of temperature, pH, and microorganism cell density sufficient to maintain the microorganism in the bioreactor in a steady state condition.

2. The process as set forth in claim 1, wherein the organic solvent compound is present in the bioreactor in a concentration therein of between about 100 ppm and 10,000 ppm.

3. The process as set forth in claim 1, wherein the organic solvent compound is introduced into the bioreactor after volatilization in an airstream.

4. The process of claim 1 wherein the radioactive isotope is tritium, C-14, S-35 or P-32.

* * * * *